United States Patent
Gunnars et al.

(10) Patent No.: US 6,770,755 B1
(45) Date of Patent: Aug. 3, 2004

(54) PROCESS OF OXIDIZING PRIMARY ALCOHOLS

(75) Inventors: Susanna Gunnars, Alnö (SE); Petter Bragd, Gothenburg (SE); Arie Cornelis Besemer, Amerongen (NL); Thomas Jaschinski, Mannheim (DE)

(73) Assignee: SCA Hygiene Products Zeist B.V., AJ Zeist (NL)

( * ) Notice: Subject to any disclaimer, the term of this patent is extended or adjusted under 35 U.S.C. 154(b) by 0 days.

(21) Appl. No.: 10/129,527

(22) PCT Filed: Nov. 8, 2000

(86) PCT No.: PCT/NL00/00812

§ 371 (c)(1), (2), (4) Date: Sep. 13, 2002

(87) PCT Pub. No.: WO01/34657

PCT Pub. Date: May 17, 2001

(30) Foreign Application Priority Data

Nov. 8, 1999 (EP) ............................................. 99203726

(51) Int. Cl.⁷ .......................... C07G 17/00; C07H 1/00; C07H 3/00; C08B 37/00
(52) U.S. Cl. .......................... 536/124; 536/56; 536/102; 536/105; 536/106
(58) Field of Search .......................... 536/56, 102, 105, 536/106, 123.1, 124

(56) References Cited

U.S. PATENT DOCUMENTS

| | | | | |
|---|---|---|---|---|
| 3,873,614 A | * | 3/1975 | Lamberti et al. | 260/535 |
| 5,334,756 A | * | 8/1994 | Likibi et al. | 562/565 |
| 6,331,619 B1 | * | 12/2001 | Besemer et al. | 536/105 |

FOREIGN PATENT DOCUMENTS

| | | | |
|---|---|---|---|
| DE | 4209869 | 10/1992 | |
| DE | 19746805 | 4/1999 | |
| WO | 95/07303 | 3/1995 | |
| WO | 99/23117 | 6/1998 | |
| WO | WO 99/23117 | * 5/1999 | ........... C08B/15/04 |
| WO | 99/23240 | 5/1999 | |
| WO | 99/52849 | 10/1999 | |

OTHER PUBLICATIONS

Anelli, P. L. et al., "Fast and selective oxidation of primary alcohols to aldehydes or to carboxylic acids and of secondary alchols to ketones mediated by oxoammonium salts under two–phase conditions." *J. Org. Chem*, [American Chemical Soc.] 52(12): 2559–2562, 1987.

Anelli, P. L.., et al., "Oxidation of Diols with Alkali Hypochlorites Catalyzed by Oxammonium Salts under Two–Phase Condidtions", *J. Org. Chem.* 54: 2970–2972, 1989.

Blumenkrantz, N., et al., "New Method for Quantitative Determination of Uronic Acids", *J. Anal. Biochem.*, [The Academic Press, Inc.] 54: 484–489, 1973.

Chang & Robyt, "Oxidation of Primary Alcohol Groups of Naturally Occurring Polysaccharides with 2,2,6,6–Tetramethyl–1Piperidine Oxommonium Ion", *J. Carbohydrate Chem.*, [Marcel Dekker, Inc.] 15(7): 819–830, 1996.

Davis & Flitsch, "Selective Oxidation of Monosaccharide Derivatives to Uronic Acids", *Tetrahedron Lett.* [Pergamon Press Ltd] 34(7): 1181–1184, 1993.

Isogai & Kato, "Preparation of polyuronic acid from cellulose by TEMPO–mediated oxidation", *Cellulose*, [Blackie Academic & Profession] XP–000986859, 5: 153–164, 1998.

de Nooy, A. E. J. et al., "Highly Selective Tempo Mediated Oxidation of Primary Alcohol Groups in Polysaccharides", *Recl. Trav. Chim. Pays–Bas*, XP–000560836, 113: 165–166, 1994.

* cited by examiner

*Primary Examiner*—James O. Wilson
*Assistant Examiner*—Patrick Lewis
(74) *Attorney, Agent, or Firm*—Burns, Doane, Swecker & Mathis, LLP

(57) ABSTRACT

In a new process for oxidizing a primary and/or secondary alcohol, an oxidizing agent is used in the presence of a di-tertiary-alkyl nitroxyl, in an aqueous reaction medium at a pH of below 7. The di-tertiary-alkyl nitroxyl is especially 4-hydroxy-TEMPO, and the process is particularly advantageous for oxidizing carbohydrates such as starch.

17 Claims, No Drawings

PROCESS OF OXIDIZING PRIMARY ALCOHOLS

The present invention relates to a process of selectively oxidising primary alcohols, in particular primary alcohol functions in monosaccharides and polysaccharides.

Oxidation of primary alcohol functions in molecules to aldehydes and/or carboxylic acids is very useful for introducing functionalities into the molecule, for example for adjusting solubility, reactivity or for providing an anchor for coupling reactions with other molecules. Especially, oxidised carbohydrates having an intact carbon skeleton, i.e. carbohydrates oxidised at the primary hydroxyl function, are advantageous for certain applications, for example as metal chelating agents, viscosifiers, carrier materials, stabilisers, and superabsorbent polymers.

There is an increasing demand for selective oxidation reactions, i.e. for exclusive or almost exclusive oxidation of primary hydroxyl groups. An attractive method for selectively oxidising primary alcohol functions was developed in the late eighties, which uses a nitroxyl compound as an intermediary oxidising agent, and hypochlorite as the ultimate oxidising agent. Anelli et al., *J. Org. Chem.* 52, 2559 (1987), and 54, 2970 (1989), reported the oxidation of alcohols and diols with sodium hypochlorite, potassium bromide and 2,2,6,6-tetramethylpiperidinyloxy (TEMPO) or 4-methoxy-TEMPO in a two-phase solvent system (dichloromethane and water) at pH 9.5. Davis and Flitsch, *Tetrahedron Lett.* 34, 1181–1184 (1993), reported the oxidation of mono-saccharides wherein the non-primary hydroxyl groups are partly protected, using the same oxidation system.

Advantageously, the TEMPO oxidations can also be carried out in non-toxic media, especially aqueous media. DE-4209869 discloses the oxidation of alkyl polyglucosides and other compounds having primary alcohol functions with hypochlorite and TEMPO in aqueous suspension at pH 8–9. De Nooy et al (WO 95/07303 and *Recl. Trav. Chim. Pays-Bas* 113 (1994) 165–166) have described the oxidation of polysaccharides using TEMPO and a hypohalite in the presence of a catalytic amount of a TEMPO or a related nitroxyl radical in an aqueous reaction medium at a pH of between 9 and 13. Similarly, DE-19746805 describes the oxidation of starch with TEMPO, hypochlorite or chlorine, and bromide at pH 7–9. Thus the oxidations always require slightly alkaline conditions (pH above 7) when normal oxidants (chlorine, hypochlorite, bromine) are used.

The TEMPO oxidation has been further developed, e.g. as to the use of alternative oxidising agents. WO 99/23117 and WO 99/23240 describe the oxidation of cellulose and starch, respectively, with TEMPO and an oxidative enzyme (laccase) and oxygen at pH 4–9 resulting in products containing low numbers of carbaldehyde and carboxyl groups. For the specific application to cellulose further research has been reported by Isogai and Kato *Cellulose* 1998, 5, 153–164, and Chang and Robyt, *J. Carbohydrate Chem.* 15, 819–830 (1996).

Although the TEMPO oxidations usually give good results in terms of yield and selectivity, the limitation to alkaline conditions is a serious drawback.

It was surprisingly found that the TEMPO-mediated oxidation of alcohols can be effected with similar selectivity of primary over secondary alcohol functions and with even improved selectivity of alcohol to aldehyde over aldehyde to carboxylic acid oxidation, by selecting specific TEMPO analogues and by carrying out the oxidation at acidic pHs (pH below 7). The pH can be as low as about 0.2, depending on the reaction conditions and the TEMPO derivative. The oxidation of primary alcohols using TEMPO with halide and peracid (peracetic acid) at pH of 5 and higher is disclaimed.

Although various TEMPO analogues can be used in the process according to the invention, preference is given to 4-hydroxy-2,2,6,6-tetramethylpiperidin-1-oxyl (4-hydroxy-TEMPO) and acylated derivatives thereof such as 4-acetoxy, 4-phosphonooxy and 4-benzoyloxy-TEMPO, as well as to 4-amino-TEMPO and acylated derivatives thereof such as 4-acetamido- and 4-maleimido-TEMPO. 4-Hydroxy-TEMPO is most preferred. Combinations of nitroxyls can also be used, for example to adjust the aldehyde to acid ratio. A suitable combination is e.g. unsubstituted TEMPO and 4-acetamido-TEMPO. Precursors can also be used. A precursor is understood to comprise a compound that under the reaction conditions can form nitroxyl radicals, such as the corresponding hydroxylamines and nitrones; the di-tert-alkyl nitroxyl may also be prepared for example by oxidation of the corresponding di-tert-alkylamine with hydrogen peroxide and tungstate. A catalytic amount of nitroxyl is preferably 0.05–15% by weight, based on the dry weight of the primary alcohol, or 0.05–15 mol % with respect to the hydroxymethyl (—$CH_2OH$) groups of the molecule, especially the carbohydrate molecule. Preferably the nitroxyl is present in an amount of 0.2–5%.

The oxidising agent can be any oxidising agent capable of reoxidising reduced nitroxyls, such as ozone and especially hypohalites. Also hydrogen peroxide or organic hydroperoxides may be used, suitably with a metal catalyst. Furthermore, peracids such as peracetic acid, and perbenzoic acid may be used without the necessity of concomitantly using halide. The amount of oxidising agent is e.g. 0.1–20 wt. %, especially 0.1–20 wt. %, preferably 0.5–7.5 wt. % with respect to the dry weight of the alcohol. The oxidation can be performed at ambient temperature or increased temperature. The oxidation should be performed at a pH between 2 and 7, especially between 3 and 6 to give best results. The reaction temperature is advantageously kept between 5° C. and 50° C.

It was furthermore found that the oxidation can be successfully performed without further oxidising agent, especially when 4-acetamido TEMPO or another 4-amido TEMPO or hydroxy-TEMPO is used under acidic conditions. Acidic conditions can be adjusted e.g. by addition of an inert organic or inorganic acid, e.g. sulphuric acid or a sulphonic acid such as toluenesulphonic acid. A lower pH, generally between 0.5 and 3, is used in this embodiment. This embodiment has the advantage that the product is free of any halogen reagent. The actual oxidising species may be the nitroxyl radical, but it may also be a disproportionation product of TEMPO, such as the nitrone. The spent TEMPO derivative can be regenerated off-line, using e.g. ozone or another oxidising agent.

Although the process can be used for introducing low levels of oxidation, it is preferred that at least 10%, more preferably at least 25% of the primary hydroxyl groups are converted to carbaldehyde groups and/or carboxylic groups. Especially the product contains both carbaldehyde groups and carboxylic groups, in a ratio of at least 1:5, preferably at least 1:2, up to e.g. 2:1.

The process according to the invention can be used for oxidising compounds having primary and/or secondary alcohol functions. The process can be used for oxidising compounds having both primary and secondary alcohol functions, such as 1,6-octanediol and, in particular, carbohydrates and their reduced derivatives (glycitols), as the process exhibits a preference of primary over secondary alcohol functions. Both monomeric carbohydrates (monosaccharides), and dimeric, oligomeric and polymeric carbohydrates, as well as sugar alcohols can be oxidised, if they have a primary alcohol function.

Examples of polymeric carbohydrates are β-glucans, such as cellulose and chitin (1,4-β), curdlan and scleroglucan and other 1,3-β-glucans and fractions, derivatives and hydrolysis products thereof, α-glucans, in particular starch (1,4-α) and pullulan (1,6/1,4/1,4-α) and fractions, derivatives and hydrolysis products thereof —such as amylose and maltodextrins-, and cyclic equivalents thereof such as cyclodextrin, also other polysaccharides such as fructans including inulin, and natural or artificial gums such as xanthan (1,4-β, with side chains), guar, carob flower, algin, gum arabic, dragacanth, agar, ghatti, carrageenin, and the like. In particular, the method is suitable for the oxidation of water-soluble oligosaccharides and polysaccharides such as starch, cellulose, galactomannans and fructans or fractions, hydrolysates or derivatives thereof. An interesting group of polysaccharides are the hydroxyalkyl (hydroxyethyl, hydroxypropyl and the like) derivatives. These can also be oxidised in the side chain, resulting in (additional) formyl-alkyl and/or carboxyalkyl derivatives. Carboxyalkyl derivatives such as carboxymethyl cellulose can also be substrates for the present process.

The products obtained by the process of the invention are characterised by the presence of carbaldehyde groups and/or carboxyl groups, depending on the reaction conditions (temperature, pH and rate of addition of oxidising agent: more aldehyde at lower temperature, lower pH and slower addition). The aldehyde to acid ratio also depends on the substrate; it is e.g. higher in starch than in short-chain glycosides. The ratio can also be influenced by the nature of the nitroxyl compound; e.g. 4-hydroxy-TEMPO gives a higher ratio than 4-acetamido-TEMPO, and the latter gives a higher ratio than unsubstituted TEMPO.

The products can be used as chelating agents for metals and the like. Oxidised polysaccharides according to the invention are also useful as absorbent materials. Especially the products containing carbaldehyde groups are useful starting materials for amino-, imino-, hydroxylamino-functionalised and other derivatives, and as crosslinkable units in e.g. the production of hydrogels and absorbing materials. If required the carbaldehyde groups can be converted to carboxyl groups by further oxidation, e.g. with alkali metal chlorite. The products can be functionalised further by oxidation, hydroxyalkylation, carboxymethylation, cationisation, crosslinking with diepoxy or diamino compounds, divinyl sulphone, trimetaphosphates or other reagents. Crosslinking is especially desired for carboxylic products in the production of absorbing polymers, and is preferably performed after the oxidation.

EXAMPLES

Example 1

In 250 ml of water 5.5 g of potato starch (4.5 g of dry substance) was gelatinized at 85° C. After cooling the solution, 150 mg of 4-hydroxy-TEMPO (Hüls, Marl in Germany) was added. The pH was brought to 3.5 by addition of acetic acid. Then 0.5 ml of a sodium hypochlorite solution (2.3 M) was added. The pH started to drop slowly and to keep the pH between 3 and 3.5 sodium hydroxide solution was added. As soon as the reaction did not proceed to a significant extent, (usually after 2 to 3 hours) 0.5 ml sodium hypochlorite solution was added. In the course of two days 10 ml of the reagent was added. After completion of the reaction the uronic acid content was measured according to the Blumenkrantz assay (Blumenkrantz et al., *J. Anal. Biochem.* 54, 484 (1973)). About 25 % of the anhydroglucose units were converted in uronic acid groups. However, a significant amount of aldehyde groups was found to be present, which was proven by subsequent oxidation with sodium chlorite. To the still viscous solution 1 gram of sodium chlorite (Aldrich, 80% purity) was added. A gradual pH increase was observed. By addition of acetic acid the pH was kept below 4. After one day the uronic acid content was measured again and was found to be 35%.

Example 2

The experiment described in Example 1 was repeated using the same amount of starch, but with 400 mg of 4-hydroxy-TEMPO. The pH was kept between 4 and 4.5. In the course of eight hours, 5 ml of sodium hypochlorite solution (2.3 M) was added. According to the Blumenkrantz assay 10% of the anhydroglucose units were converted into uronic acid. After reaction with sodium chlorite to determine the total degree of primary oxidation, the uronic acid content was increased to 15%. Examples 1 and 2 were not optimised as to total degree of oxidation.

Example 3

The experiment described in Example 1 was repeated using the same amount of starch, but now the pH was kept at between 4.8 and 5.0. In the course of six hours sodium hypochlorite was added (0.5 ml per time; in total 15 ml was added). After 18 hours the reaction was finished (no further sodium hydroxide consumption was observed). According to the Blumenkrantz assay 40% of the anhydroglucose units were converted to uronic acid. By treatment of the reaction product with sodium chlorite/hydrogen peroxide the aldehyde groups present were converted into the acid. To the reaction mixture a solution of hydrogen peroxide (Merck, 1.0 ml 30% w/w) and 1.0 g of sodium chlorite (Aldrich, 80% purity) were added. A reaction occurred, which was noticeable from the oxygen evolution and from the pH drop, i.e. after an initial raise due to the alkaline reaction of sodium chlorite the pH started to drop within a few minutes. The pH was kept at 4.5 by addition of 0.5 M sodium hydroxide solution. Before sodium chlorite addition the consumption of sodium hydroxide was 13.2 ml 0.5 M. After completion of the reaction the total consumption was 23.5 ml 0.5 M. According to the uronic acid assay, the content of uronic acid was 55%. This means that the ratio aldehyde/acid in this experiment after this conversion was 3:4.

Example 4

In 100 ml of water 18 mg of 4-acetoxy TEMPO (prepared from 4-hydroxy-TEMPO by reaction with acetic anhydride for one day at room temperature) and 1.1 g of methyl glucopyranoside (5.7 mmol; Aldrich) were dissolved. To the reaction mixture 0.5 ml of sodium hypochlorite solution was added portion wise (0.1 ml). The pH was kept between 4.8 and 5. After the reaction was finished, apparent from the fact that no further pH drop was observed , 0.1 ml of a 30% hydrogen peroxide solution (Merck, p.a.) was added, followed by 400 mg of sodium chlorite (Aldrich, 80% purity). A fast reaction occurred, which was seen by oxygen evolution and pH drop. The pH was kept at 5 by adding sodium hydroxide solution. After a few hours the reaction stopped. According to the Blumenkrantz method 2.9 mmol of uronic acid was formed.

Example 5

In 50 ml of water 20 mg of 4-acetoxy TEMPO and 1.1 g of α-methylglucopyranoside were dissolved. To this solution 3.5 ml of sodium hypochlorite solution (2.3M) was added. During reaction the pH was kept between 5 and 6 by addition of 0.5 M NaOH solution. After completion of the reaction 0.2 ml hydrogen peroxide solution (Merck, 30% w/w) and 400 mg of sodium chlorite (Aldrich) were added. After a small pH increase, the pH dropped from 5 to 4.5. According to the Blumenkrantz method 3.2 mmol of uronic acid was present.

Example 6

In 70 ml of water 150 mg 4-hydroxy TEMPO and 1.1 g I α-methylglucopyranoside (Aldrich, 99% purity) were dissolved. Sodium hypochlorite solution was added (in total 5 ml 2.3 M). The pH was kept constant at 5 by adding a sodium hydroxide solution. After completion of the reaction, apparent from the fact that no farther NaOH had to be added, 2.2 mmol NaOH was consumed. Then 0.20 ml of hydrogen peroxide solution and 0.50 g of sodium chlorite (80%, Aldrich) were added. The pH started to drop and in the course of three hours an additional 1.4 mmol NaOH were added to keep pH at 5. From these ratios it follows that the ratio acid: aldehyde is about 1.5: 1. According to the Blumenkrantz assay the 4.6 mmol of uronic acid was formed.

Example 7

In 100 ml of water 70 mg of 4-acetamido-TEMPO and 2.04 g of MGP were dissolved. In the course of a few hours portion wise sodium hypochlorite solution was added. To keep the pH at 5 0.5 M sodium hydroxide solution was added. The sodium hydroxide consumption after consumption of 6 ml of sodium hypochlorite was 5.05 mmol. Then, to complete the conversion into carboxylic acid groups 0.20 ml of hydrogen peroxide solution and 0.50 g of sodium chlorite (80%, Aldrich) were added. The reaction mixture was allowed to react for 20 hours. Finally the uronic acid content was measured according to the Blumenkrantz method. The yield was 5.5 mmol., which is in agreement with the amount of sodium hydroxide consumed.

Example 8

In 100 ml of water 125 mg of 4-acetamido-TEMPO and 5.54 g of potato starch were dissolved. In the course of a few hours sodium hypochlorite solution was added. The pH was kept at 5 by adding 0.5 M sodium hydroxide solution. The sodium hydroxide consumption after consumption of 15 ml of sodium hypochlorite (34.5 mmol) was 12.3 ml (6.15 mmol). Then, to complete the conversion to carboxylic acid groups 1.0 ml of hydrogen peroxide solution and 1000 mg of sodium chlorite (80%, Aldrich) were added sodium chlorite was added. The reaction mixture was allowed to react for 20 hours. The total NaOH consumption was 22.9 ml (11.45 mmol) Finally the uronic acid content was measured according to the Blumenkrantz method. The yield was 11 mmol, which is in agreement with the amount of sodium hydroxide consumed. This points to a ratio of aldehyde to acid of 1:1.2.

Example 9

To potato starch (8.3 g dry substance in 400 ml water) 0.1 ml of acetic acid and 400 mg 4-hydroxy TEMPO, a sodium hypochlorite solution (2.1 M) was added in quantities of 0.2 ml per time. This resulted in a slight pH increase. In the course of about 10 minutes the pH decreased again to 5. After the pH did not decrease anymore, again sodium hypochlorite was added and this was repeated until 12 ml (25.2 mmol) was added. The sodium hydroxide consumption after complete oxidation amounted 6.5 mmol (I) of uronic acid. The solution was subsequently treated with sodium chlorite and hydrogen peroxide. After addition of 2 ml 30% hydrogen peroxide solution (w/w), 5 g $NaClO_2$ (Aldrich, 80%) was added in the course of 20 minutes. The pH was brought to pH 4.5 by addition of acetic acid and was maintained at this value by addition of sodium hydroxide solution. The total consumption was 19 mmol. According to the Blumenkrantz assay, in solution (I) 9.3 mmol of uronic acid and in solution (II) 19 mmol of uronic acid was present.

The mixture was concentrated to a volume of 200 ml and poured out into 400 ml of ethanol. A gummy precipitate was formed, from which the liquid was decanted, after standing for one day. After removal of the residual ethanol by passing a nitrogen stream the 6-carboxy starch (with a degree of oxidation of 35%) was dissolved in 18 ml of water, the pH was adjusted to 4.7 and 400 mg of butanediol diglycidyl ether was added. The highly viscous solution was heated at 50° C. during 20 hours. During heating the viscosity increased and finally a gel was obtained. After washing and drying a material as obtained which had an FSC in synthetic urine (0.13 M NaCl, 0.06 M KCl, 1.8% urea, 2 mM $CaSO_4$, 3.5 mM of $MgSO_4$ and 0.1% Triton X in water) of 20 g/g; centrifuge retention capacity at 300 g: 16 g/g.

Example 10

A solution of 1.0 g (5.1 mmol) of α-methylglucopyranoside and 2.2 g of 4-acetamido-TEMPO in 100 ml of water was brought to pH 2 and then allowed to react for 20 hours. According to the Blumenkrantz assay 0.6 mmol of glucuronic acid was formed. The pH was brought to 4 and 0.1 ml of hydrogen peroxide (30% w/w) and 400 mg $NaClO_2$ were added. A gradual decrease in pH was observed and to keep the pH at 4 NaOH (1.0 mmol) had to be added. After the reaction was finished the uronic acid was increased to 2.0 mmol. Based on these measurements a total degree of oxidation of 39% was attained with a 1:1 aldehyde/acid ratio.

Example 11

A solution of 300 mg 4-hydroxy-TEMPO and 220 mg of α-methylglucopyranoside in 10 ml of water was brought to pH 1.9 and then allowed to react for 24 hours. After one day 8 mg of uronic acid was present. After reaction with sodium chlorite (150 mg) and hydrogen peroxide (0.10 ml 30% w/w) at pH 4, the uronic acid content was increased to 16 mg (8% conversion).

Example 12

A solution of 400 mg TEMPO and 250 mg of α-methylglucopyranoside in 80 ml of water was brought to pH 1.17 and then allowed to react for 2 hours. During standing the pH decreased slightly. The final pH value was 1.03. The pH was then brought to 5 and sodium chlorite (150 mg) and hydrogen peroxide (0.10 ml 30% w/w) were added. After one day the uronic acid content was measured (65 mg, which corresponds to a degree of oxidation of 25%).

Example 13

A solution of 0.1 g (0.5 mmol) of α-methylglucopyranoside and 55 mg of 4-acetamido-TEMPO in 100 ml of water was adjusted to pH 1.5 by addition of concentrated sulphuric acid. The solution was allowed to react for 48 hours at 20° C. The carbonyl content was determined using high performance anionic exchange chromatography (HPAEC) with amperometric detection using DIONEX pulsed electrochemical detector (PED). The primary C6 aldehyde was the only product that was detected. Consequently, no overoxidation to carboxylates had occurred. The ratio of C aldehyde to unreacted glucopyranoside according to the chromatogram was 0.07 (about 7% conversion).

Example 14

Example 13 was repeated, however with a pH adjusted to 0.5. Again, no other product than the C6 aldehyde was detected. The ratio of C aldehyde to unreacted glucopyranoside according to the chromatogram was 0.19 (about 16% conversion).

What is claimed is:

1. A process for oxidising a carbohydrate or a reduced, hydroxyalkylated or carboxyalkylated carbohydrate derivative comprising oxidising the carbohydrate or a reduced, hydroxyalkylated or carboxyalkylated carbohydrate derivative in an aqueous reaction medium at a pH below 7 using an oxidising agent consisting essentially of a hypohalite, hydrogen peroxide or ozone in the presence of a di-tertiary-alkyl nitroxyl.

2. A process according to claim 1, wherein the nitroxyl is 4-hydroxy-2,2,6,6-tetra-methyl-piperidin-1-oxyl or an ester thereof, or 4-alkanoylamido-2,2,6,6-tetra-methyl-piperidin-1-oxyl.

3. A process according to claim 1, wherein the nitroxyl is used in a catalytic amount of 0.05–25% based on the alcohol.

4. A process according to claim 1, wherein a pH of 3–6 is used.

5. A process according to claim 1 wherein the carbohydrate is a polysaccharide or a hydroxyalkyl polysaccharide.

6. A process according to claim 5, wherein the polysaccharide is starch or cellulose, or a fraction, a hydrolysis product or a reduced, hydroxyalkylated or carboxyalkylated derivative thereof.

7. A process according to claim 6, wherein a pH of between 4.5 and 6.5 is used for oxidising starch, and a pH between 3 and 6 is used for oxidising cellulose.

8. A process according to claim 5, wherein the polysaccharide is oxidised to an extent that it contains on average at least 0.3 aldehyde, ketone and/or carboxyl groups per monosaccharide unit.

9. A process according to claim 5, in which the polysaccharide is crosslinked prior to the oxidation.

10. A process according to claim 1, wherein the nitroxyl is used in a catalytic amount of 0.2–10% based on the alcohol.

11. A process according to claim 5, wherein the polysaccharide is oxidised to an extent that it contains on average at least 0.1 aldehyde group per monosaccharide unit.

12. A process according to claim 5, wherein the polysaccharide is oxidised to an extent that it contains on average at least 0.2 aldehyde group per monosaccharide unit.

13. A process according to claim 5, in which the polysaccharide is crosslinked subsequently to the oxidation.

14. A process according to claim 1, wherein the oxidising agent consists essentially of a hypohalite in the presence of a di-tertiary-alkyl nitroxyl.

15. A process according to claim 1, wherein the oxidising agent consists essentially of hydrogen peroxide in the presence of a di-tertiary-alkyl nitroxyl.

16. A process according to claim 1, wherein the oxidising agent consists essentially of ozone in the presence of a di-tertiary-alkyl nitroxyl.

17. A process according to claim 1, wherein the oxidised carbohydrate or reduced, hydroxyalkylated or carboxyalkylated carbohydrate derivative contains on average at least 0.1 aldehyde group per monosaccharide unit.

* * * * *